(12) United States Patent
Coric et al.

(10) Patent No.: US 12,102,618 B2
(45) Date of Patent: *Oct. 1, 2024

(54) USE OF RILUZOLE PRODRUGS TO TREAT ATAXIAS

(71) Applicant: Biohaven Therapeutics Ltd., New Haven, CT (US)

(72) Inventors: Vladimir Coric, Madison, CT (US); Robert Berman, New Haven, CT (US); Melissa Beiner, Madison, CT (US); Gilbert L'Italien, Deep River, CT (US)

(73) Assignee: Biohaven Therapeutics Ltd., Tortola (VG)

(*) Notice: Subject to any disclaimer, the term of this patent is extended or adjusted under 35 U.S.C. 154(b) by 0 days.

This patent is subject to a terminal disclaimer.

(21) Appl. No.: 18/353,840

(22) Filed: Jul. 17, 2023

(65) Prior Publication Data
US 2023/0390252 A1    Dec. 7, 2023

Related U.S. Application Data

(63) Continuation of application No. 16/762,165, filed as application No. PCT/US2018/060232 on Nov. 11, 2018.

(60) Provisional application No. 62/717,948, filed on Aug. 13, 2018, provisional application No. 62/584,856, filed on Nov. 12, 2017.

(51) Int. Cl.
| | |
|---|---|
| *A61K 31/428* | (2006.01) |
| *A61P 25/00* | (2006.01) |
| *A61K 9/20* | (2006.01) |
| *A61K 9/48* | (2006.01) |

(52) U.S. Cl.
CPC ............ *A61K 31/428* (2013.01); *A61P 25/00* (2018.01); *A61K 9/20* (2013.01); *A61K 9/48* (2013.01)

(58) Field of Classification Search
CPC .............................. A61K 31/428; A61P 25/00
See application file for complete search history.

(56) References Cited

FOREIGN PATENT DOCUMENTS

WO    WO-2016140878 A2 *   9/2016    ........... A61K 9/2004

OTHER PUBLICATIONS

Ristori et al., Neurology 2010; vol. 74: pp. 839-845. (Year: 2010).*
Romano et al, Lancet Neurol 2015; 14: pp. 985-991. (Year: 2015).*
Copending U.S. Appl. No. 16/762,165, filed May 7, 2020. (Year: 2020).*
Bezprozvanny et al., Drugs Future 2009, vol. 34(12), pp. 1-17. (Year: 2009).*
Gribkoff, V.K. & Kaczmarek, L.K. "The Need for New Approaches in CNS Drug Discovery: Why Drugs Have Failed, and What Can Be Done to Improve Outcomes," 2017, Neuropharmacology, 120, pp. 11-19.
Perlman, S.L. "Update on the Treatment of Ataxia: Medication and Emerging Therapies," 2020, Neurotherapeutics, 17, pp. 1660-1664.
"Biohaven Provides Update on Phase 3 Clinical Trial Evaluating Troriluzole for Spinocerebellar Ataxia (SCA)" Retrieved from the Internet; <URL: https://www.prnewswire.com/news-releases/biohaven-provides-update-on-phase-3-clinical-trial-evaluating-troriluzole-for-spinocerebellar-ataxia-sca-301552633.html>; Retrieved on Oct. 19, 2023.

* cited by examiner

*Primary Examiner* — Craig D Ricci
*Assistant Examiner* — Janet L Coppins
(74) *Attorney, Agent, or Firm* — Wiggin and Dana LLP

(57) ABSTRACT

Disclosed are methods of treating ataxia by administering to a patient in need thereof a riluzole prodrug such as troriluzole. Pharmaceutical compositions and kits including the riluzole prodrugs are also disclosed.

13 Claims, No Drawings

USE OF RILUZOLE PRODRUGS TO TREAT ATAXIAS

CROSS-REFERENCE TO RELATED APPLICATIONS

This application is a continuation of U.S. patent application Ser. No. 16/762,165 filed May 7, 2020, which is a national stage application under 35 U.S.C. § 371 of International Application No. PCT/US2018/060232 filed Nov. 11, 2018, which claims priority to U.S. Provisional Application No. 62/584,856 filed Nov. 12, 2017 and U.S. Provisional Application No. 62/717,948 filed Aug. 13, 2018, and all the benefits accruing therefrom under 35 U.S.C. § 119, the contents of all of which applications are incorporated herein in their entireties by reference.

FIELD OF THE INVENTION

The present invention relates to the use of prodrugs of riluzole to treat ataxias such as Spinocerebellar ataxia and Friedreich ataxia.

BACKGROUND OF THE INVENTION

Ataxia is a disorder of the central nervous system wherein the patient is unable to coordinate muscles for the execution of voluntary movement, see, e.g., Klockgether, T., Ataxias, Parkinsonism and Related Disorders, 13, S391-S394, 2007. Typical symptoms of ataxia are gait dysfunctions, imbalance, impaired limb coordination and altered speech. In many ataxia disorders, the ataxia is due to degeneration of the cerebellar cortex and its afferent or efferent fiber connections. Typical affected brain regions are cerebellum, posterior column, pyramidal tracts and basal ganglia. Ataxia may lead to a decreased motoneuron function. Ataxia is typically classified into hereditary and non-hereditary ataxias.

Hereditary ataxias are further classified into autosomal recessive and autosornal dominant ataxias. Autosomal recessive ataxias are, for example, Friedreichs ataxia ("FA"), Ataxia telangiectasia ("AT"), Autosomal recessive ataxia with oculomotor apraxia type 1, Autosomal recessive ataxia with oculomotor apraxia type 2, Spinocerebellar ataxia with axonal neuropathy, Abetalipoproteinemia, Ataxia with isolated vitamin E deficiency, Refsums disease and Cerebrotendinous xanthomatosis. Autosomal dominant ataxias include, for example, Spinocerebellar ataxia ("SCA"), which can be further classified into ataxias associated with translated GAG repeat expansions (SCA 1, 2, 3, 6, 7 and 17), ataxias associated with untranslated repeat expansions in non-coding regions (SCAB, 10 and 12), ataxias associated with point-mutations (SCA5, 13, 14 and 27). SCA3 is also known as Machado-Joseph disease.

Non-hereditary ataxias can be further classified into degenerative and acquired ataxias. Degenerative ataxias are, for example, multiple system atrophy ataxia and sporadic adult-onset ataxia. Acquired ataxias can be, for example, associated with alcoholic/toxin-caused cerebellar degeneration or paraneoplastic cerebellar degeneration.

There are currently no U.S. Food and Drug Administration ("FDA") approved medications for the treatment of SCAs. The diagnosis of a spinocerebellar ataxia requires the exclusion of acquired, non-genetic causes of ataxia, including alcoholism, vitamin deficiencies, multiple sclerosis, vascular disease, tumors, and paraneoplastic disease. A definitive diagnosis requires genetic testing or occurrence within a kindred. Lifespan is often significantly shortened due to complications related to neurologic deficits.

Common features among the SCAs include being associated with spinocerebellar degeneration, which is often observable on brain imaging. In addition, symptom presentation among the SCA subtypes share many common, prominent features: slowly progressive, symmetrical, midline and appendicular ataxia with dysmetria, i.e., loss of accuracy; dysdiadochokinesis, i.e., loss of rhythm as in difficulty performing alternating movements; decreased speed of eye movements that affect eye gaze (including nystagmus and diplopia); abnormalities of speech, i.e., dysarthria; difficulty swallowing; hand/foot incoordination, i.e., limb ataxia; abnormal station; and, abnormal gait. Notably, there can also be significant clinical variation in the order and/or extent of symptom expression between mutations, within a common mutation, and even within a kindred that shares the same genotype. Non-cerebellar involvement may also occur in many SCA subtypes (e.g., cognition, pyramidal, extrapyramidal, motor neuron, peripheral nerve or macular involvement).

Signs and symptoms of SCA typically begin in early adulthood, but can appear anytime from childhood to late adulthood; SCAs are degenerative and progress over a number of years. The severity of the disability and related mortality depends on type of ataxia, the age of onset of symptoms, and other factors that are poorly understood at this time. It is common for subsequent generations to experience earlier onset and more extensive disease, attributable to the phenomenon of "anticipation" whereby mutation length, e.g., polyglutamine triplet expands over successive generations.

The typical clinical course of SCAs may be described, for example, as follows. Balance and coordination are often affected first. Incoordination of hands, arms, and legs, and slurring of speech are other common, early symptoms. Over time, individuals with SCA may develop numbness, tingling, or pain in the arms and legs, i.e., sensory neuropathy, uncontrolled muscle tensing, i.e., dystonia, muscle wasting, i.e., atrophy, and muscle twitches, i.e., fasciculations.

Walking often becomes difficult and is characterized by walking with feet placed further apart to compensate for poor balance. Impaired coordination of the arms and hands can affect the ability to perform tasks requiring fine motor control such as writing and eating. Rarely, rigidity, tremors, and involuntary jerking movements, i.e., chorea, have been reported in people who have been affected for many years.

Slow eye movements can be seen in some forms of ataxia, including weakness in the muscles that control eye movement, i.e., ophthalmoplegia. As time goes on, ataxia can affect speech and swallowing. Finally, individuals with SCA may also have difficulty processing, learning, and remembering information, i.e., cognitive impairment.

With the production of abnormal proteins, the affected nerve cells often eventually begin to function poorly and ultimately degenerate. As SCA progresses, muscles can become decreasingly coordinated, causing ataxia symptoms to become more pronounced.

The most common SCAs include type 1, 2, 3, 6, 7, 8 and 10. SCA1 often produces gait ataxia, limb ataxia, and dysarthria, with brainstem involvement but little cognitive abnormality. SCA2 is notable for the association of ataxia and dysarthria with slow saccadic eye movements and polyneuropathy. SCA3 (Machado-Joseph disease) is often accompanied by eyelid retraction, reduced blinking, external ophthalmoplegia, dysarthria, dysphagia, and sometimes parkinsonism or peripheral neuropathy. SCA6 is comparatively less severe, typically progresses more slowly, is more limited to cerebellar involvement than other SCAs, and has a later age of onset. SCA7 is distinguished by retinal degeneration leading to blindness, in addition to ataxia. Overall, there is significant symptom overlap among these SCAs. The shared symptomatic manifestations of the SCAs may reflect common pathology affecting cerebellar purkinje cell fibers.

Glutamate is a predominant excitatory neurotransmitter responsible for regulating signaling in normal brain function. Riluzole (6-(trifluoromethoxy)benzothiazol-2-amine) is a glutamate modulator which has been used for treatment of amyotrophic lateral sclerosis (ALS).

Riluzole has been studied in patients with hereditary cerebellar ataxias at doses of 50 milligrams ("mg") orally, twice daily (see, Romano et al., Lancet Neurol 2015; 14: 985-91, and ClinicalTrials.gov, number NCT01104649). On page 985 of the Romano et al., publication, it is stated that:

Our findings lend support to the idea that riluzole could be a treatment for cerebellar ataxia. Longer studies and disease-specific trials are needed to confirm whether these findings can be applied in clinical practice.

Accordingly, new methods are desired for the treatment of ataxia which may provide benefits for patients afflicted with the disease.

SUMMARY OF THE INVENTION

The present invention is directed to the treatment of ataxia, e.g., SCA, with prodrugs of riluzole. By virtue of the present invention, it may now be possible to provide more effective ataxia treatments to patients. Patients may experience an improved response in one or more areas including, for example, overall survival, quality of life, overall response rate, duration of response, delay of onset, or patient reported outcome.

In one aspect of the invention, there is provided a method of treating ataxia in a patient in need thereof, comprising administering to the patient a therapeutically effective amount of a riluzole prodrug.

In one aspect, the ataxia is one or more of Friedreichs ataxia ("FA"), Ataxia telangiectasia ("AT"), Autosomal recessive ataxia with oculomotor apraxia type 1, Autosomal recessive ataxia with oculomotor apraxia type 2, Spinocerebellar ataxia with axonal neuropathy, Abetalipoproteinemia, Ataxia with isolated vitamin E deficiency, Refsums disease and Cerebrotendinous xanthomatosis.

In one aspect, the ataxia is Spinocerebellar ataxia ("SCA") selected from SCA1, SCA2, SCA3, SCA6, SCA7, SCA8 and SCA10.

In one aspect, the ataxia is one or more of an ataxia associated with translated GAG repeat expansions (SCA 1, 2, 3, 6, 7 and 17), an ataxia associated with untranslated repeat expansions in non-coding regions (SCAB, 10 and 12), or an ataxia associated with point-mutations (SCA5, 13, 14 and 27).

In one aspect, the ataxia is a multiple system atrophy ataxia or a sporadic adult-onset ataxia.

In one aspect, the riluzole prodrug has the following formula:

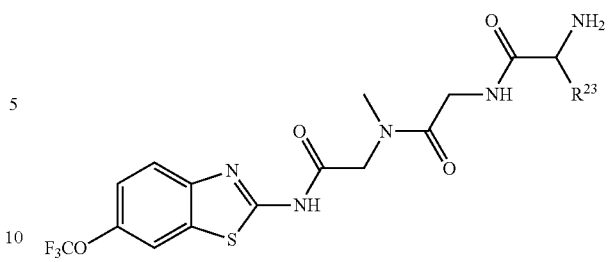

and pharmaceutically acceptable salts thereof, wherein:
$R_{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$.

In one aspect, the riluzole prodrug has the following formula:

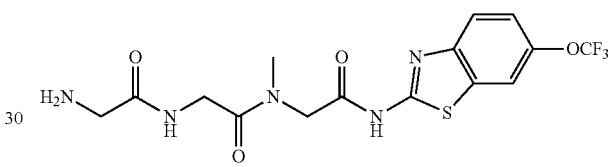

In one aspect, the treatment provides an improvement in the patient's total SARA score of at least 0.8, or 0.9, or 1.0, or 1.1, or 1.2, or 1.3, or 1.4, or 1.5, or 1.6, or 1.7, or 1.8, or 1.9, or 2.0, or greater.

In one aspect, the riluzole prodrug is administered to the patient at a dosage of from about 17.5 to 200 mg per day.

In one aspect, the riluzole prodrug is administered to the patient at a dosage of about 17.5, or 35, or 70, or 100, or 140, or 200 mg per day.

In one aspect, the riluzole prodrug is administered to the patient at a dosage of 200 mg, once per day.

In one aspect, the riluzole prodrug is administered to the patient at a dosage of 100 mg, twice per day.

In one aspect, the riluzole prodrug is administered to the patient at a dosage of 140 mg, once per day.

In one aspect, the riluzole prodrug is administered to the patient at a dosage of 70 mg, twice per day.

In one aspect, the riluzole prodrug is administered to the patient once per day.

In one aspect, the riluzole prodrug is administered to the patient twice per day.

In one aspect, the riluzole prodrug is administered to the patient in the form of a capsule.

In one aspect, the riluzole prodrug is administered to the patient in the form of a tablet.

In one aspect, the riluzole prodrug is administered to the patient for a duration of from about 8 weeks to 48 weeks.

In one aspect, the riluzole prodrug is administered to the patient for a duration of from about 8 weeks to 16 weeks.

In one aspect of the invention, there is provided a method for improving a response in a patient afflicted with ataxia comprising administering to the patient in need thereof, an effective amount of a riluzole prodrug.

In one aspect, the improved response is one or more of overall survival, quality of life, overall response rate, duration of response, delay of onset, or patient reported outcome.

In one aspect, the improved response is one or more of an improvement of gait, balance, limb coordination or speech.

In one aspect, the improved response is an increased period of time between episodes of ataxia.

In one aspect of the invention, there is provided a kit for treating a patient afflicted with ataxia, the kit comprising:
(a) a riluzole prodrug; and
(b) instructions for administering the riluzole prodrug in the method of the invention.

DETAILED DESCRIPTION OF THE INVENTION

The following detailed description is provided to aid those skilled in the art in practicing the present invention. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting.

As used in this application, except as otherwise expressly provided herein, each of the following terms shall have the meaning set forth below. Additional definitions are set forth throughout the application. In instances where a term is not specifically defined herein, that term is given an art-recognized meaning by those of ordinary skill applying that term in context to its use in describing the present invention.

The articles "a" and "an" refer to one or to more than one (i.e., to at least one) of the grammatical object of the article unless the context clearly indicates otherwise. By way of example, "an element" means one element or more than one element.

The term "about" refers to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition.

The term "administering" refers to the physical introduction of a composition comprising a therapeutic agent to a subject, using any of the various methods and delivery systems known to those skilled in the art. Typical routes of administration for riluzole prodrugs include oral administration, e.g., by capsule or tablet. Administering can also be performed, for example, once, a plurality of times, and/or over one or more extended periods and can be a therapeutically effective dose or a subtherapeutic dose.

The term "dosing frequency" refers to the frequency of administering doses of a formulation disclosed herein in a given time. Dosing frequency can be indicated as the number of doses per a given time, e.g., once a week or once in two weeks.

The term "effective amount" refers to that amount which is sufficient to effect an intended result. The effective amount will vary depending on the subject and disease state being treated, the severity of the affliction and the manner of administration, and may be determined routinely by one of ordinary skill in the art.

The terms "in combination with" and "in conjunction with" refer to administration of one treatment modality in addition to another treatment modality. As such, "in combination with" or "in conjunction with" refers to administration of one treatment modality before, during, or after administration of the other treatment modality to the subject.

The term "pharmaceutically acceptable salt" refers to a salt form of one or more of the compounds or prodrugs described herein which are presented to increase the solubility of the compound in the gastric or gastroenteric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art.

The term "prodrug" refers to a precursor of a drug which may be administered in an altered or less active form. The prodrug may be converted into the active drug form in physiological environments by hydrolysis or other metabolic pathways. A discussion of prodrugs is provided in T. Higuchi and V. Stella, Pro-drugs as Novel Delivery Systems (1987) 14 of the *A.C.S. Symposium Series*, and in Bioreversible Carriers in Drug Design, (1987) Edward B. Roche, ed., American Pharmaceutical Association and Pergamon Press.

The terms "subject" and "patient" refer any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

The terms "therapeutically effective amount", "therapeutically effective dosage" and "therapeutically effective dose" of an agent (also sometimes referred to herein as a "drug") refers to any amount of the active agent that, when used alone or in combination with another agent, protects a subject against the onset of a disease or promotes disease regression evidenced by a decrease in severity of disease symptoms, an increase in frequency and duration of disease symptom-free periods, or a prevention of impairment or disability due to the disease affliction. The therapeutically effective amount of an agent can be evaluated using a variety of methods known to the skilled practitioner, such as in human subjects during clinical trials, in animal model systems predictive of efficacy in humans, or by assaying the activity of the agent in in vitro assays.

The term "treatment" refers to any treatment of a condition or disease in a subject and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii)

ameliorating or relieving the conditions caused by the disease, i.e., symptoms of the disease. Treatment could be used in combination with other standard therapies or alone. Treatment or "therapy" of a subject also includes any type of intervention or process performed on, or the administration of an agent to, the subject with the objective of reversing, alleviating, ameliorating, inhibiting, slowing down or preventing the onset, progression, development, severity or recurrence of a symptom, complication or condition, or biochemical indicia associated with a disease.

Riluzole is currently available in the market as RILUTEK® (riluzole) is available from Sanofi-Aventis, Bridgewater, NJ and has the structure shown below.

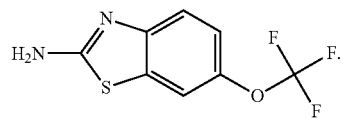

6-(trifluoromethoxy)benzothiazol-2-amine

Certain preferred riluzole prodrugs have the structure:

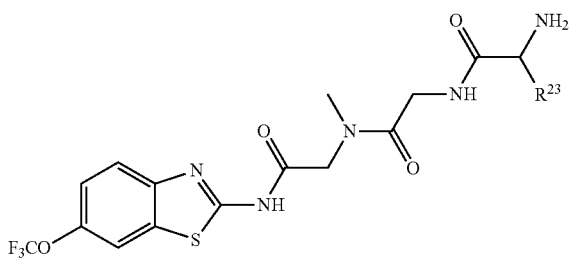

including enantiomers, diastereomers, hydrates, solvates, pharmaceutically acceptable salts, and complexes thereof, wherein:

$R_{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$. Such agents may be useful as part of the combination of the present invention.

One especially preferred riluzole prodrug, troriluzole (also known as "trigriluzole"), has the following formula:

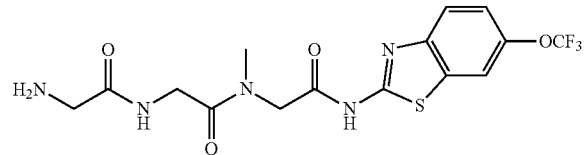 [SMILES: CN(CC(=O)Nc1nc2ccc(OC(F)(F)F)cc2s1)C(=O)CNC(=O)CN]

Prodrugs of riluzole are described, for example, in U.S. patent application Ser. No. 14/385,551, U.S. patent application Ser. No. 14/410,647, PCT Application Serial No. PCT/US2016/019773 and PCT Application Serial No. PCT/US2016/019787.

The riluzole prodrugs may be present as isotopically labeled forms of compounds detailed herein. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}S$, $^{35}S$, Cl and I. Various isotopically labeled compounds of the present disclosure, for example those into which radioactive isotopes such as $^3H$, $^{13}C$ and $^{14}C$ are incorporated, are provided. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans). Also provided for isotopically labeled compounds described herein are any pharmaceutically acceptable salts, or hydrates, as the case may be.

In some variations, the compounds disclosed herein may be varied such that from 1 to "n" hydrogens attached to a carbon atom is/are replaced by deuterium, in which "n" is the number of hydrogens in the molecule. Such compounds may exhibit increased resistance to metabolism and are thus useful for increasing the half-life of the compound when administered to a subject. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved drug metabolism and pharmacokinetics (DMPK) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure can generally be prepared by carrying out the procedures known to those skilled in the art by substituting a readily available isotopically labeled reagent for a non-isotopically labeled reagent. It is understood that deuterium in this context is regarded as a substituent in the compounds provided herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The riluzole prodrugs of the present invention may be given orally, sublingually, intranasally, buccally, subcutaneously or in any other suitable means of delivery.

The dose of the riluzole prodrug to be administered may depend on the subject to be treated inclusive of the age, sex, weight and general health condition thereof. In this regard, precise amounts of the agent(s) for administration will depend on the judgment of the practitioner. In determining the effective amount of the riluzole prodrug to be administered in the treatment or reducing of the conditions associated with the symptoms and disorders, the physician may evaluate clinical factors including symptoms severity or progression of the disorder. The effective amount of the treatment will vary depending on the subject and disease state being treated, the severity of the affliction and the manner of administration, and may be determined routinely by one of ordinary skill in the art.

The riluzole prodrug for treating ataxia or symptoms may be dosed at or below about 400 mg/day, at or below about 300 mg/day, at or below about 200 mg/day, at or below about 150 mg/day, at or below about 100 mg/day, at or below about 70 mg/day, at or below about 60 mg/day, at or below about 50 mg/day, at or below about 42.5 mg/day, at or below about 37.5 mg/day at or below about 35 mg/day, at or below about 20 mg/day, at or below about 17.5 mg/day, at or below about 15 mg/day, at or below about 10 mg/day, at or below about 5 mg/day, or at or below about 1 mg/day. In one aspect, the riluzole prodrug is administered to the patient at a dosage of from about 17.5 to 200 mg per day, preferably about 17.5, or 35, or 70, or 100, or 140, or 200 mg per day.

Typical dosing frequencies for the riluzole prodrugs include once a day, twice a day, three times a day, four times a day, once every other day, once a week, twice a week, three times a week, four times a week, once every two weeks, once or twice monthly, and the like. The dosing frequency is typically once per day, e.g., 140 mg per dose, or twice per day, e.g., 70 mg per dose, when administered orally for ingestion.

The pharmaceutical compositions of the present invention comprising the riluzole prodrug typically also include other pharmaceutically acceptable carriers and/or excipients such as binders, lubricants, diluents, coatings, disintegrants, barrier layer components, glidants, coloring agents, solubility enhancers, gelling agents, fillers, proteins, co-factors, emulsifiers, solubilizing agents, suspending agents and mixtures thereof. A skilled artisan in the art would know what other pharmaceutically acceptable carriers and/or excipients could be included in the formulations according to the invention. The choice of excipients would depend on the characteristics of the compositions and on the nature of other pharmacologically active compounds in the formulation. Appropriate excipients are known to those skilled in the art (see Handbook of Pharmaceutical Excipients, fifth edition, 2005 edited by Rowe et al., McGraw Hill) and have been utilized to yield a novel sublingual formulation with unexpected properties.

Examples of pharmaceutically acceptable carriers that may be used in preparing the pharmaceutical compositions of the present invention may include, but are not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, polyvinylpyrrolidone (PVP), talc, calcium sulphate, vegetable oils, synthetic oils, polyols, alginic acid, phosphate buffered solutions, emulsifiers, isotonic saline, pyrogen-free water and combinations thereof. If desired, disintegrating agents may be combined as well, and exemplary disintegrating agents may be, but not limited to, cross-linked polyvinyl pyrrolidone, agar, or alginic acid or a salt thereof such as sodium alginate. In general, the pharmaceutical compositions of the present invention may be manufactured using methods known in the art, for example, by means of conventional mixing, dissolving, granulating, dragee-making, levigating, emulsifying, encapsulating, entrapping, lyophilizing processes and the like.

The pharmaceutical compositions of the present invention may be administered in any suitable dosage form which can be determined by those skilled in the art. Typical dosage forms include tablets and capsules for oral ingestion, orally dissolving or disintegrating tablets or films for sublingual, buccal or other mucosal administration, transdermal patches, and the like.

In one aspect of the invention, the riluzole prodrug is provided in a form of an orally dissolving or disintegrating tablet (ODT) for sublingual administration. In general, the excipients, including mannitol and gelatin, are blended, solubilized with water and deaerated before being mixed with the active pharmaceutical ingredient (API), which has been milled separately. The particle size of the API (D50) is less preferably than about 2 microns. The mixture is lyophilized by flash freezing and then freeze-dried. The effective amount of riluzole prodrug for the sublingual formulation useful in the present invention to achieve a therapeutically effective dose may be less than that of orally administered agent. For example, the effective dose of the sublingual formulation of the riluzole prodrug may be about 1 to 95%, preferably 50 to 90%, more preferably 70 to 85% and most preferably about 80% of that of the orally administered agent in a conventional tablet or capsule. In one aspect of the invention, the pharmaceutical compositions are prepared in an ODT form as described in U.S. Pat. No. 9,192,580, issued Nov. 24, 2015. ODT dosage forms are further described by Gregory et al., U.K. Patent No. 1,548,022 using fish gelatin as the carrier. Fish gelatins suitable for use in the invention are commercially available.

Typically, the ODT dosage form disintegrate or disperse within 1 to 60 seconds, preferably 1 to 30 seconds, more preferably 1 to 10 seconds and particularly 2 to 8 seconds, after being placed in contact with a fluid. The fluid is preferably that found in the oral cavity, i.e., saliva, as with oral administration.

The ODT compositions according to the invention can also contain, in addition to the active ingredient arid fish gelatin carrier, other matrix forming agents and secondary components. Matrix forming agents suitable for use in the present invention include materials derived from animal or vegetable proteins, such as other gelatins, dextrins and soy, wheat and psyllium seed proteins; gums such as acacia, guar, agar, and 10 xanthan; polysaccharides; alginates; carboxymethylcelluloses; carrageenans; dextrans; pectins; synthetic polymers such as polyvinylpyrrolidone; and polypeptide/protein or polysaccharide complexes such as gelatin-acacia complexes.

Other materials which may also be incorporated into the ODT compositions of the present invention include sugars such as mannitol, dextrose, lactose, galactose, and trehalose; cyclic sugars such as cyclodextrin; inorganic salts such as sodium phosphate, sodium chloride and aluminum silicates; and amino acids having from 2 to 12 carbon atoms such as glycine, L-alanine, L-aspartic acid, L-glutamic acid, L-hydroxyproline, L-isoleucine, L-leucine and L-phenylalanine. One or more matrix forming agents may be incorporated into the solution or suspension prior to solidification (freezing). The matrix forming agent may be present in addition to a surfactant or to the exclusion of a surfactant. In addition to forming the matrix, the matrix forming agent may aid in maintaining the dispersion of any active ingredient within the solution of suspension. This is especially helpful in the case of active agents that are not sufficiently soluble in water and must, therefore, be suspended rather than dissolved. Secondary components such as preservatives, antioxidants, surfactants, viscosity enhancers, coloring agents, flavoring agents, pH modifiers, sweeteners or taste-masking agents may also be incorporated into the fast-dissolving compositions. Suitable coloring agents include red, black and yellow iron oxides and FD & C dyes such as FD&C Blue No. 2 and FD&C Red No. 40 available from Ellis & Everard. Suitable flavoring agents include mint, raspberry, licorice, orange, lemon, grapefruit, caramel, vanilla, cherry and grape flavors and combinations of these. Suitable pH modifiers include the edible acids and bases, such as citric acid, tartaric acid, phosphoric acid, hydrochloric acid, maleic acid and sodium hydroxide. Suitable sweeteners include, for example, sucralose, aspartame, acesulfame K and thaumatin. Suitable taste-masking agents include, for example, sodium bicarbonate, ion exchange resins, cyclodextrin inclusion compounds, adsorbates or microencapsulated actives.

In a preferred aspect of the invention, the ODT compositions comprises from about 50-70 wt % riluzole prodrug, about 10-30 wt % fish gelatin, about 10-20 wt % of one or more fillers, and 0.1-5.0 wt % of one or more flavorants.

Other methods of preparing ODTs may be used without limitation, and detailed description of general methods thereof have been disclosed, for example, in U.S. Pat. Nos. 5,631,023; 5,837,287; 6,149,938; 6,212,791; 6,284,270; 6,316,029; 6,465,010; 6,471,992; 6,471,992; 6,509,040; 6,814,978; 6,908,626; 6,908,626; 6,982,251; 7,282,217; 7,425,341; 7,939,105; 7,993,674; 8,048,449; 8,127,516; 8,158,152; 8,221,480; 8,256,233; and 8,313,768.

One measure for assessment of the methods of the present invention is by using the Scale for the Assessment and Rating of Ataxia ("SARA").

The SARA was developed as a clinician-administered instrument to measure severity of symptoms in patients with SCA. While there are multiple scales available, the SARA has been tested in many patients with SCA. It has been demonstrated to have excellent inter-rater reliability [i.e., intraclass correlations of >0.95 (61, 62)], good test-retest reliability [intraclass coefficient of 0.90 (61)], high internal consistency [Cronbach's alpha of >0.94 (61, 62)], sensitivity to change over time in populations with SCA (2, 63, 64) and able to detect treatment effects (65). In addition, the SARA scores were highly correlated with measures of activities of daily living, such as the Barthel Index (typically used in stroke) and the Unified Huntingtons Disease Rating Scale Part IV (typically used in Huntingtons Disease).

The SARA scores range from 0 (no ataxia) to 40 (severe). The SARA takes approximately 15 minutes to administer. Assessed items include:
  Gait (rated 0 to 8)
  Stance (0 to 6)
  Sitting (0 to 4)
  Speech disturbance (0 to 6)
  Finger chase (0 to 4)
  Nose-finger test (0 to 4)
  Fast alternating hand movements (0 to 4)
  Heel-shin slide (0 to 4)

Once each of the 8 categories has been assessed, the total score is calculated to determine the severity of ataxia. For motor activities of the four extremities (items 5-8), assessments are performed bilaterally and the mean values are used to obtain the total score.

Other assessments that can be used to measure the effectiveness of the methods of the present invention include the following.

8-Meter Walk Test

Advantages of performance-based measures include are that metric outcomes are amenable to quantitative analysis; are associated with high inter-rater reliability; and, these particular tasks are not prone to learning/training effects. In addition, these tests assess core functional deficits with ataxia, insofar as fundamental symptoms involve deficits with lower (e.g., walking) and upper extremity coordination (e.g., fine hand skills). The 8 Meter Walk Test (time in seconds to walk 8 meters at fastest speed without personal assistance). This task is performed twice.

9-Hole Peg Test

In this test, subjects place/remove pegs from the Rolyan 9-hole peg test apparatus for each hand separately. The task is assessed twice for both the dominant and non-dominant hand. The outcome measure is time (seconds).

The Inventory of Non-Ataxia Symptoms (INAS)

The INAS was designed for the purpose of assessing the non-ataxia symptoms that are commonly associated with the inherited cerebellar ataxias. This is a clinician administered scale that consists of 30 items that assess 16 symptom domains:
  Reflexes: biceps, patellar, Achilles, extensor plantar reflex;
  Motor Symptoms: spasticity, paresis, muscle atrophy, fasciculations, myoclonus, rigidity, chorea/dyskinesia, dystonia, resting tremor;
  Sensory Symptoms: impaired vibration sense;
  Ophthalmological findings: fixation/smooth pursuit, fast saccades, visual acuity;
  Reported abnormalities: double vision, dysphagia, urinary dysfunction, cognitive impairment (examiner impression).

Unified Huntigton's Disease Rating Scale Part IV (Functional Assessment)

The Unified Huntington's Disease Rating Scale (UHDRS) is a clinical rating scale originally developed to assess multiple domains in subjects with the neurodegenerative illness, Huntington's Disease. One validated domain (UHDRS-IV) is the Functional Assessment subscale and its use has been validated in populations with ataxia (68) in general and SCA (61, 68, 69) specifically. The UHDRS-IV assesses 25 instrumental and basic activities of daily living.

Sheehan Disability Scale (SDS)

The Sheehan Disability Scale (SDS) is a patient-rated measure of functional disability in domains of work, social and family life. The SDS has demonstrated sensitivity to treatment effects in numerous randomized controlled trials in populations with varied diagnoses. The assessment is a three item questionnaire measuring disease-related disruption of work, social life and family life. Respondents evaluate impairment on an 11 point scale: "not at all", three categories of "mild", three categories of "moderate", three categories of "marked", and "extreme".

The EQ-5D

The EQ-5D is a patient self-report general health outcome measure comprised of multiple domains. Sensitivity of symptom improvement is uncertain. Domains of the EQ-5D include:
  Mobility;
  Self-care;
  Usual daily activities;
  Pain/Discomfort;
  Anxiety/Depression
  Visual Analog Scale rating of overall health
  Clinical Global Impression-Global Improvement (CGI-I)
  This is a 7-point scale that requires the clinician to assess how much the subject's illness has improved or worsened relative to the baseline visit and it is rated as follows:
    very much improved
    much improved
    minimally improved
    no change minimally worse
much worse
very much worse Patient Global Impression of Change (PGI-C)

This is a patient self-reported global index scale that may be used to rate the response of a condition to a therapy.

Cerebellar Neuropsychiatric Rating Scale (CNRS)

Based on an emerging understanding of the role of the cerebellum in neuropsychiatric pathology, the Cerebellar Neuropsychiatric Rating Scale (CNRS) was developed. This scale is completed by the informant. Key symptom domains include attentional control, emotional control, autism spectrum symptoms, psychosis spectrum symptoms and social skill set. Each domain is assessed by 4 to 9 questions by a collateral informant. There are a total of 35 questions, each with 4 response categories (1-never, 2-sometimes, 3-often, and 4-almost always). Each domain receives a sub-score and a total score is summed from all domains.

Cognitive Test Battery

The Cerebellar Cognitive Affective Schmahmann Syndrome Scale (CCAS) is a clinician administered tool that assesses neurocognitive functions that are considered mediated, at least partially, by the cerebellum: executive function (planning, set-shifting, abstract reasoning, working memory, and decreased verbal fluency), linguistic function (dysprosodia, agrammatism and mild anomia), spatial cognition (Visual spatial organization and memory), and personality (affective range, disinhibition). The test battery takes approximately 15 minutes to administer and includes specific pencil and paper tests that have been shown to assess deficits in subjects with cerebellar pathology.

Ophthalmological Assessments (SCA 7 ONLY)

Subjects with SCA7 can undergo quantitative ophthalmologic assessments by either an ophthalmologist or qualified technician:

Best corrected visual acuity (right eye and left eye measurements): Visual acuity is affected in SCA7 and is therefore be measured longitudinally. This test is to be applied with the ETDRS chart (either back-illuminated or projected) with the patient's correction for distance.

Color vision: SCA7 is often characterized by cone-rod dystrophy affecting color vision. Therefore, color vision is be assessed longitudinally, specifically via a Farnsworth D15 Arrangement Test. Testers (i.e., ophthalmologists or qualified technicians) complete a score sheet, which is used to generate a number of parameters, including Total Error Score, Selectivity Index, and Confusion Index.

Multifocal Electroretinogram (mfERG): mfERG measures electrical responses in the retina from different retinal locations. In SCA7, mfERG commonly shows loss of photopic function suggestive of diminished cone photoreceptors. Key parameters include P1 amplitude and P1 timing in both the right and left eyes for each of the 5 measured rings.

Tonometry: This test assesses intraocular pressure at baseline. The preferred method utilizes applanation tonometry.

Also, within the scope of the present invention are kits comprising a riluzole prodrug (e.g., riluzole) for therapeutic uses. Kits typically include a label indicating the intended use of the contents of the kit and instructions for use. The term label includes any writing, or recorded material supplied on or with the kit, or which otherwise accompanies the kit.

EXAMPLES

The following examples illustrate the invention and are not intended to limit the scope of the invention.

Example 1

A clinical study is conducted with the following parameters. For additional information, refer to ClinicalTrials.gov Identifier NCT02960893, www.clinicaltrials.gov.

Trial in Adult Subjects With Spinocerebellar Ataxia

The purpose of this study is to compare the efficacy of BHV-4157 versus placebo on ataxia symptoms in subjects with spinocerebellar ataxia (SCA).

| Condition | Intervention | Phase |
| --- | --- | --- |
| Spinocerebellar Ataxias | Drug: BHV-4157Drug: | Phase 2 |
| Spinocerebellar Ataxia Type 1 | Placebo Comparator | Phase 3 |
| Spinocerebellar Ataxia Type 2 | | |
| Spinocerebellar Ataxia Type 3 | | |
| Spinocerebellar Ataxia Type 6 | | |
| Spinocerebellar Ataxia Type 7 | | |
| Spinocerebellar Ataxia Type 8 | | |
| Spinocerebellar Ataxia Type 10 | | |

Study Type: Interventional
Study Design: Allocation: Randomized
  Intervention Model: Parallel Assignment
  Masking: Quadruple (Participant, Care Provider, Investigator, Outcomes Assessor)
  Primary Purpose: Treatment
Official Title: A Phase IIb/III, Randomized, Double-blind, Placebo-controlled Trial of BHV-4157 in Adult Subjects With Spinocerebellar Ataxia
Primary Outcome Measures:
  To measure the change in total score on the Scale for Assessment and Rating of Ataxia (SARA) [Time Frame: The change in total score from baseline to week 8.]
Secondary Outcome Measures:
  To assess the safety and tolerability of BHV-4157 in subjects with SCA by measuring the frequency and severity of adverse events and discontinuations of adverse events. [Time Frame: Baseline to week 8.] Measured by the frequency and severity of adverse events and discontinuations of adverse events.
  To compare efficacy of BHV-4157 with placebo on patient impression of benefit via use of the PGI-C [Time Frame: Baseline to Week 8] Change in PGI-C score

| Estimated Enrollment: 120 | |
| --- | --- |
| Arms | Assigned Interventions |
| Experimental: BHV-4157 140 mg QD | Drug: BHV-4157 140 mg capsule QD |
| Placebo Comparator: Placebo Comparator matching placebo capsule QD | Drug: Placebo Comparator |

| Eligibility | |
| --- | --- |
| Ages Eligible for Study: | 18 Years to 75 Years (Adult, Senior) |
| Sexes Eligible for Study: | All |
| Accepts Healthy Volunteers: | No |

Criteria
Inclusion Criteria:
  Subjects with a known or suspected diagnosis of the following specific hereditary ataxias: SCA1, SCA2, SCA3, SCA6, SCA7, SCA8 and SCA10
  Ability to ambulate 8 meters without assistance (canes and other devices allowed)
  Screening total SARA total score ≥8
  Determined by the investigator to be medically stable at baseline/randomization and must be physically able and expected to complete the trial as designed
  Subjects must have adequate hearing, vision, and language skills to perform SARA ratings, 8 Meter Walk Test and other neuropsychiatric testing and interviews as specified in the protocol
Exclusion Criteria:
  Any medical condition other than one of the hereditary ataxias specified in the inclusion criteria that could predominantly explain or contribute significantly to the subjects' symptoms of ataxia
  MMSE score <24
  SARA total score of >30 points at screening
  Clinical history of stroke
  Active liver disease or a history of hepatic intolerance to medications that in the investigator's judgment, is medically significant
Additional Exploratory Objectives Include:
Exploratory Objectives
  To compare the efficacy of BHV-4157 with placebo on non-ataxia symptoms in subjects with SCA after 8 weeks of treatment, via assessment on the INAS
  To assess pharmacokinetics of BHV-4157 and riluzole as well as assess their correlations with clinical outcome measures
  To compare efficacy of BHV-4157 with placebo on the 9-hole peg test
  To compare the efficacy of BHV-4157 with placebo on disability as measured by the Sheehan Disability Scale (SDS)
  To compare efficacy of BHV-4157 with placebo on health outcomes via use of the EQ-5D
  To compare efficacy of BHV-4157 with placebo on patient impression of benefit via use of the PGI-C
  To compare efficacy of BHV-4157 with placebo on clinician impression of benefit via use of the CGI-I
  To compare efficacy of BHV-4157 with placebo on activities of daily living, as assessed via the UHDRS-IV (the functional subscale of the UHDRS)
  To assess correlations of SCA Genotype with treatment effect
  In the subgroup with SCA7, to provide preliminary assessments on effects of BHV-4157 on ophthalmological assessments
  To compare efficacy of BHV-4157 with placebo on the Cerebellar Neuropsychiatric Ratings Scale (CNRS) and its subdomains
  To compare efficacy of BHV-4157 with placebo on cognitive function, as measured by the Cerebellar Cognitive Affective Schmahmann Syndrome Scale (CCAS)
  To compare the effects of BHV-4157 with placebo on changes in plasma BDNF and proBDNF levels
  To compare the effects of BHV-4157 with placebo on the video-recorded assessment of the gait item (Item 1) of the SARA, as assessed by a blinded rater
The Study Design is as Follows:
  The study is a Phase IIb/III, multicenter, randomized, double-blind, 2-arm placebo-controlled parallel-group study designed to assess safety, tolerability, and efficacy signals in a population of patients with Spinocerebellar Ataxia (SCA). Subjects will be randomized to receive placebo (QD) or BHV-4157 (140 mg QD), stratified by diagnosis (genotype) and baseline severity (Gait Item of the SARA of ≤4 and >4). Subjects with SCA3 genotype will be limited to comprise up to approximately 10% of the total population so that this most common type of SCA is not over-represented.
  Dosing will continue for 8 weeks. Subjects will return to the clinic two weeks after discontinuing study medication for a follow-up safety visit. In addition, subjects completing the Randomization Phase will be offered 48 weeks of open-label treatment as long as the PI believes open-label treatment offers an acceptable risk-benefit profile. Subjects who agree to enter the Extension Phase will not be required to wash-out of drug or complete the follow-up safety visit, but instead should continue dosing as specified in the extension phase. Subjects entering the Extension Phase would have their first Extension Visit four weeks after the Week 8 Randomization Phase visit. If there is a delay of two weeks or more in dosing between the Randomization Phase and the Extension Phase, subjects will be required to complete an Extension Baseline Visit. Thereafter, subjects will undergo visits every fourth week through Week 12 of this phase. Then subjects will undergo visits every 12 weeks up to Week 48 of this phase. All subjects will undergo a post study drug termination visit two weeks after the last dose of study drug in the Extension Phase.
  Subjects will receive placebo (QD) or BHV-4157 (140 mg QD) loose filled capsule. It is recommended that all patients ingest this drug once every day in the morning (approximately at the same time each day), without regard to meals. If subjects have difficulty tolerating morning dosing (such as experiencing sedation) then the investigator may permit the subject to switch to nighttime dosing (and document this change).
  Tables 1 to 7 below show data from Example 1.

TABLE 1

STABLE Subjects, defined by SCR-to-BLSARA within 1 point[#]
Stable baseline defined as Total SARA scores at screening and baseline within the group median of 1 point, comprising 63 subjects (49% of total sample)

|  | BHV-4157 | Placebo | ΔBtw Groups [95% CI] | Response Definition | BHV-4157 | Placebo | *p-value |
|---|---|---|---|---|---|---|---|
| Total SARA STABLE | −0.90 (n = 34) | −0.50 (n = 29) | −0.39 [−1.2-0.45] | ≥3 points | 24% | 3.4% | 0.03 |
| Total SARA UNSTABLE | −0.87 (n = 28) | −1.49 (n = 38) | 0.62 [−0.61-1.85] | ≥ 1 point | 59% | 41% | 0.21 |

TABLE 1-continued

STABLE Subjects, defined by SCR-to-BLSARA within 1 point[#]
Stable baseline defined as Total SARA scores at screening and baseline within the group median
of 1 point, comprising 63 subjects (49% of total sample)

|  | STABLE | | NOT- STABLE | |
| --- | --- | --- | --- | --- |
|  | BHV-4157 (n = 34) | Placebo (n = 29) | BHV-4157 (n = 28) | Placebo (n = 38) |
| Total SARA | −0.90 | −0.50 | −0.87 | −1.49 |
| Axial SARA [#1-4] | −0.27 | 0.18 | −0.46 | −0.48 |
| Appendicular SARA [4-8] | −0.36 | −0.44 | −0.15 | −0.69 |

*fisher exact test without correction for multiple comparisons
[#] ≤ 1 point on Total SARA score 1

TABLE 2

Population selected based on Experience of Site/Raters
Sites selected on the basis that the Principal Investigator has over two
decades of ataxia research and Pls are raters, represents 72 subjects
(55% of total sample)

|  | BHV-4157 (n = 37) | Placebo (n = 35) | Δ Btw Groups [95% CI] |
| --- | --- | --- | --- |
| Total SARA | −1.37 | −0.97 | −0.40 [−1.3-0.52] |
| Gait [#1] | −0.14 | −0.06 | −0.08 [−0.29-0.14] |
| Axial Items [#1-4] | −0.47 | 0.05 | −0.52 [−1.1-0.07] |
| Appendicular [#5-8] | −0.52 | −0.68 | 0.16 [−0.39-0.72] |

| Response Definition | BHV-4157 | Placebo | *p-value |
| --- | --- | --- | --- |
| ≥3 points | 21.6% | 5.7% | 0.09 |
| ≥1 point | 51.4% | 31.4% | 0.10 |

*analytic model identical to primary, presenting LSmeans
*fisher exact test without correction for multiple comparisons

TABLE 3

Population selected based on Experience of Site/Raters

|  | BHV-4157 (n = 37) | Placebo (n = 35) | Δ Btw Groups [95% CI] |
| --- | --- | --- | --- |
| Total SARA | −1.37 | −0.97 | −0.40 [−1.3-0.52] |
| Gait [#1] | −0.14 | −0.06 | −0.08 [−0.29-0.14] |
| Axial Items [#1-4] | −0.47 | 0.05 | −0.52 [−1.1-0.07] |
| Appendicular [#5-8] | −0.52 | −0.68 | 0.16 [−0.39-0.72] |

*analytic model identical to primary, presenting LSmeans
*Assuming true difference from data above, 500 subjects per arm would be required to provide 90% power for a randomized controlled trial
A study this large is prohibitive for orphan indication and presents challenges in detecting signals at 8-weeks
Placebo effects may extinguish over long-term
Longitudinal cohort can be compared to Natural History Cohort to demonstrate neuro-protective effects

TABLE 4

Exposure Proxy: Weight (lighter)
Sample divided by median weight (≤76.4 kg vs >76.4 kg)
Lighter median had crude preliminary estimate of 40% greater exposure
(using unmodeled data) and Phase 1 studies show correlation of weight with exposure

| Lighter median | BHV-4157 (n = 27) | Placebo (n = 39) | ΔBtw Groups [95% CI] |
| --- | --- | --- | --- |
| Total SARA* | −1.38 | −0.89 | −0.50 [−1.6-0.60] |
| Axial Items [1-4] | −0.85 | −0.49 |  |
| Appendicular Items [5-8] | −0.69 | −0.46 |  |

|  | Change in Total SARA Score | | | Responder Analysis | | | |
| --- | --- | --- | --- | --- | --- | --- | --- |
| Efficacy Sample | BHV-4157 | Placebo | ΔSARA [95% CI] | Response Definition | BHV-4157 | Placebo | P-value* |
| All Lighter Subjects | −1.38 (n = 27) | −0.89 (n = 39) | −0.50 [−1.6-0.60] | ≥3 points in All Subjects (n = 65) | 33% | 18% | 0.24 |
| Stable Subgroup | −1.18 (n = 19) | −0.35 (n = 17) | −0.83 | ≥3 points at Experienced sites (n = 36) | 26% | 0 | 0.05 |
| EXP Sites | −1.64 (n = 18) | −0.61 (n = 19) | −1.03 | ≥3 points in Stable Subjects (n = 36) | 39% | 5% | 0.02 |

*fisher exact test without correction for multiple comparisons

TABLE 5

Exposure Proxy: Weight
Examination of PGIC and CGI - no correlation or trend in general
population or general subpopulations
Trends in lighter weight sample (from total subset and among
experienced sites)

| | Sample | BHV-4157 | Placebo |
|---|---|---|---|
| CGI | | | |
| Any Improvement | Lighter | 64% (n = 22) | 45% (n = 29) |
| Much Improved | " | 27% | 796 |
| Any Improvement | Lighter at EXP sites | 60% (n = 15) | 33% (n = 12) |
| Much Improved | " | 14% | 3% |
| PGI | | | |
| Any Improvement | Lighter | 34% (n = 23) | 20% (n = 29) |
| "Better and Definite Improvement that has made a real & worthwhile difference" | " | 17% | 0 |
| Any Improvement | Lighter at EXP sites | 45% (n = 16) | 8% (n = 12) |
| Better and Definite . . . | " | 19% | 0 |

TABLE 6

Gender as proxy for Exposure
Females have greater may have approximately 50% greater exposure based
on Phase 1 data (c/w Rilutek USPI)

| | Change in Total SARA Score | | Responder Analysis | | |
|---|---|---|---|---|---|
| Females | BHV-4157 | Placebo | Response Definition | BHV-4157 | Placebo |
| All Subjects | −1.08 (n = 31) | −0.83 (n = 36) | ≥3 points in All Subjects (n = 67) | 32% | 17% |
| STABLE Subgroup | −1.33 (n = 18) | −0.40 (n = 15) | ≥3 points at Experienced sites (n = 33) | 39% | 0 |
| Experience of Sites | −1.15 (n = 20) | −0.64 (n = 18) | ≥3 points in Stable Subjects (n = 38) | 35% | 6% |

TABLE 7

Gender as proxy for Exposure

| | Females Subjects in Stable Subgroup | | | Females Subjects in Experienced Site Group | |
|---|---|---|---|---|---|
| Response Definition | BHV-4157 (n = 18) | Placebo (n = 15) | Response Definition | BHV-4157 (n = 17) | Placebo (n = 18) |
| ≥3 points | 39% | 0 | ≥3 points | 41% | 6% |
| ≥1 point | 67% | 33% | ≥1 point | 71% | 28% |

Example 2

This example describes a study entitled: Interim Extension Phase Analyses of Study BHV4157-201: Phase IIb/III, Randomized, Double-blind, Placebo-controlled Trial of Troriluzole (BHV-4157) in Adult Subjects with Spinocerebellar Ataxia followed by 96-Week Open-Label Extension Phase.

Introduction/Background:

Hereditary Spinocerebellar Ataxias (SCA) are progressive neurodegenerative disorders that are characterized clinically by progressive ataxia and are attributed to various autosomal dominant genetic mutations. Currently, there are no FDA medications approved for this debilitating disorder and treatment remains supportive. The shared symptomatic manifestations of the SCAs may reflect common pathology affecting cerebellar purkinje cell fibers. Prior studies suggest that riluzole, via multiple mechanisms, including glutamate modulation, may improve a range of genetically determined ataxias, potentially by affecting Purkinje excitability. Troriluzole (BHV-4157; formerly trigriluzole) is a novel pro-drug of riluzole. An on-going PhaseIIb/III study, BHV4157-201, is predicated on preclinical and clinical studies that implicate a role for troriluzole in the potential treatment of SCA.

As previously reported, in the primary analysis from the 8-week Randomization Phase of the trial troriluzole showed numerical improvement on the total score on the Scale for Assessment and Rating of Ataxia (SARA) at Week 8 but did not meet the study criteria in differentiating from placebo; however, post-hoc analyses showed trends for therapeutic benefit in relevant subgroups (e.g., those projected to have higher exposures, those with stable pre-randomization baseline SARA scores). In addition, data from the randomization phase of the trial suggested a systematic difference in response between the appendicular items and the axial SARA items. When the primary analytic method was applied to the axial items and appendicular items separately, the appendicular items appear particularly sensitive to a placebo effect. To date, all subjects have had the chance to complete the Week 24 visit from the long term, open-label extension phase of the trial. In this presentation, results are presented on the course of the population up to Week 48.

Study Design:

BHV4157-201 is an on-going Phase IIb/III, multicenter, randomized, double-blind, 2-arm placebo-controlled parallel-group study designed to assess safety, tolerability, and efficacy in a population of patients with Spinocerebellar Ataxia (SCA). The study is comprised of two periods: an 8-week randomization period, followed by a 96-week open-label extension period. Regarding key entry criteria, subjects were male and female outpatients between the ages of 18-75 years, inclusive, with a known or suspected diagnosis of the following hereditary ataxias: SCA1, SCA2, SCA3, SCA6, SCA7, SCA8 and SCA10. All subjects completed genetic testing to confirm the diagnosis of hereditary ataxias. The primary objective of the study is to compare the efficacy of troriluzole versus placebo on ataxia symptoms in patients with SCA as measured by the total score on the Scale for the Assessment and Rating of Ataxia (SARA). Secondary objectives include assessments of functional disability, non-ataxia symptoms associated with SCA, global functioning, performance-based measures of ataxia, and neuropsychiatric and cognitive functioning.

During the 8-week Randomization Phase of the study, which has been completed, 141 subjects were randomized, in a 1:1 ratio, to receive either BHV-4157 (140 mg daily) or Placebo. Subjects completing the Randomization Phase were offered approximately 96 weeks of open-label treatment, provided the investigator believed open-label treatment offered an acceptable risk-benefit profile. 131 subjects entered the Extension Phase of the study, which is currently on-going.

Results:

The ongoing, open-label, extension phase of BHV4157-201 has high participation rates (99% of those completing the double-blind randomization phase; N=131) and subjects who have completed up to 48 weeks of treatment demonstrate continued improvement from Week 8 and baseline. Interim analyses based on the design adaptations described above show a consistent change in score for the axial items of the SARA (modified SARA) for all treated patients at various time points as compared to randomization baseline (Table 8). Notably, at week 24 and also week 48, subjects had a decrease of −0.40 (STDV=1.17 and 1.08, respectively) in modified SARA scores. Including analysis at 8 weeks and 36 weeks, these improvements were slightly higher in patients with lower weight and female gender. See also Tables 9-14 which show scores for various subgroups.

TABLE 8

Modified SARA change from Randomization Baseline - All Patients

| Time Period | N | Mod SARA change (SD) |
| --- | --- | --- |
| 8 weeks | 126 | −0.4 (1.50) |
| 24 weeks | 113 | −0.3 (1.35) |
| 36 weeks | 102 | −0.1 (1.30) |
| 48 weeks | 96 | −0.0 (1.44) |

TABLE 9

Modified SARA change from Randomization Baseline - Low Weight Subgroup

| Time Period | N | Mod SARA change (SD) |
| --- | --- | --- |
| 8 weeks | 63 | −0.6 (1.56) |
| 24 weeks | 58 | −0.5 (1.44) |
| 36 weeks | 54 | −0.3 (1.34) |
| 48 weeks | 50 | −0.2 (1.41) |

TABLE 10

Modified SARA change from Randomization Baseline - Female Subgroup

| Time Period | N | Mod SARA change (SD) |
| --- | --- | --- |
| 8 weeks | 64 | −0.3 (1.48) |
| 24 weeks | 59 | −0.4 (1.32) |
| 36 weeks | 54 | −0.1 (1.41) |
| 48 weeks | 50 | −0.1 (1.50) |

TABLE 11

Modified SARA change from Randomization Baseline - by SCA1 & SCA2

| Time Period | N | Mod SARA change (SD) |
| --- | --- | --- |
| 8 weeks | 65 | −0.5 (1.47) |
| 24 weeks | 60 | −0.4 (1.45) |
| 36 weeks | 57 | −0.1 (1.20) |
| 48 weeks | 54 | 0.1 (1.44) |

TABLE 14

Modified SARA change from Randomization Baseline - by Non-SCA1 & SCA2

| Time Period | N | Mod SARA change (SD) |
| --- | --- | --- |
| 8 weeks | 58 | −0.3 (1.58) |
| 24 weeks | 53 | −0.3 (1.24) |
| 36 weeks | 45 | −0.1 (1.44) |
| 48 weeks | 42 | −0.2 (1.44) |

The observed changes provide consistent sustained improvements or lack of decline in modified SARA scores at all time periods and across sub-groups (the low-weight and female being suggestive of a dose/weight response). This change also contrasts with an increase of +0.99 (STDV=2.04) in axial SARA score as described in the natural history study by Ashizawa et al at 1 year (1). From the derived minimum clinically important difference (MCID) of 0.75, these observed changes with troriluzole treatment infer a benefit exceeding the MCID.

Conclusions:

Studies in SCA suggest a mechanistic role for the glutamate modulator troriluzole in the treatment of patients with hereditary spinocerebellar ataxia. Preliminary analyses, including data from both the randomization phase and long-term extension phase of the BHV4157-201 trial, suggest a sustained, clinically relevant disease modifying treatment benefit of troriluzole relative to the natural disease progression at all follow-up time periods. While the natural history study by Ashizawa et al at 1 year shows an approximately +1 point worsening in the axial SARA score of patients with hereditary ataxias, the current ongoing trial shows a −0.1 point improvement in the axial SARA score of study participants at 6 months and no decline at 48 weeks. See, Ashizawa T, Figueroa K, Perlman S, Gomez C, Wilmot G, Schmahmann J, Ying S, Zesiewicz T, Paulson H, Shokkottai V, Bushara K, Kuo S, Geschwind M, Xia G, Mazzoni P, Krischer J, Cuthbertson D, Holbert A, Ferguson J, Pulst S, Subramony S. Clinical characteristics of patients with spinocerebellar ataxias 1, 2, 3 and 6 in the US; a prospective observational study. Orphanet J Rare Dis. 2013; 8: 177. These trends are consistent with results from two prior positive studies using the active metabolite of troriluzole. See, Ristori G, Romano S, Visconti A, Cannoni S, Spadaro M, Frontali M, Pontieri F E, Vanacore N, Salvetti M. Riluzole in cerebellar ataxia: a randomized, double-blind, placebo-controlled pilot trial. Neurology. 2010; 74(10):839-45; and Romano S, Coarelli G, Marcotulli C, Leonardi L, Piccolo F, Spadaro M, Frontali M, Ferraldeschi M, Vulpiani M C, Ponzelli F, Salvetti M, Orzi F, Petrucci A, Vanacore N, Casali C, Ristori G. Riluzole in patients with hereditary cerebellar ataxia: a randomized, double-blind, placebo-controlled trial. Lancet Neurol. 2015; 14(10):985-91. Epub 2015/09/01. doi: 10.1016/s1474-4422(15)00201-x. PubMed PMID: 26321318. Based on the totality of this data and the favorable tolerability profile of troriluzole, the Applicant believes that troriluzole may offer benefit to patients with SCA and is initiating further clinical trials with this investigational agent. Study design improvements will be incorporated into future trials based upon our Phase 2 trial experience including utilization of a modified SARA scale, enhanced rater training procedures, enrichment of trial population with particular genotypes and extension of study endpoints.

Table 15, below. It can be seen that the Modified SARA attenuates the placebo effect, and shifts the difference in favor of BHV-4157 ('all SCA'). The differences are slightly greater in SCA1&SCA2 but the combination of stability and SCA1+2 subtype yields the largest difference between BHV-4157 and placebo. Table 16 shows the eight week change from baseline. For the enriched geneotypes, the stable 2 group showed a change in SARA score of 0.24 (−0.387-−0.083) and the stable group 1 showed a change in SARA score of 0.20 (−0.286-−0.083).

TABLE 15

| | | | | | Modified SARA | | | | | |
|---|---|---|---|---|---|---|---|---|---|---|
| | | | | | | | SCA1 and SCA2 | | | |
| | Total SARA | | All SCA | | | | Stable (−1 < diff < 1) | | Stable (−1 < diff < 1) | |
| Visit | BHV | PBO | BHV | PBO | BHV | PBO | BHV | PBO | BHV | PBO |
| | | | | | May-18 | | | | | |
| Baseline | | | n = 71 | n = 68 | | | | | | |
| | | | 4.127 | 4.426 | | | | | | |
| | | | 2.177 | 2.268 | | | | | | |
| | n = 139 | | n = 139 | | | | | | | |
| | 14.230 | | 4.426 | | | | | | | |
| | 4.465 | | 2.212 | | | | | | | |
| week 8 | | | | | | | | | | |
| Δ | n = 63 | n = 68 | n = 63 | n = 68 | n = 33 | n = 36 | n = 31 | n = 27 | n = 14 | n = 12 |
| Mean | −0.810 | −1.103 | −0.429 | −0.382 | −0.424 | −0.361 | −0.387 | −0.148 | −0.286 | −0.083 |
| SD | 1.765 | 2.28 | 0.946 | 1.305 | 1.062 | 1.457 | 0.955 | 1.134 | 0.914 | 1.379 |
| StdChg | 0.459 | 0.483 | 0.453 | 0.293 | 0.399 | 0.248 | 0.405 | 0.131 | 0.313 | 0.060 |
| | | | | | Sep-17 | | | | | |
| week 8 | | | | | | | | | | |
| Δ | n = 63 | n = 68 | | | | | | | | |
| Mean | −0.810 | −1.106 | | | | | | | | |
| SD | 1.765 | 2.322 | | | | | | | | |
| StdChg | 0.459 | 0.456 | | | | | | | | |

TABLE 16

8 WEEK CHANGE FROM BASELINE

| | | | Enriched Genotypes | |
|---|---|---|---|---|
| | Total SARA. | Mod SARA. | Stable 2 | Stable 1 |
| Value-BHV5157 | −0.81 | −0.429 | −0.387 | −0.286 |
| Value-Placebo | −1.103 | −0.382 | −0.148 | −0.083 |

STABLE 1 = 1 unit change between Baseline & Screening total SARA
STABLE 2 = 2 unit change between baseline and screening total SARA Example 4

A clinical study is conducted with the following parameters. For additional information, refer to ClinicalTrials.gov Identifier NCT03701399, www.clinicaltrials.gov.

BHV-4157 in Adult Subjects With Spinocerebellar Ataxia

The purpose of this study is to compare the efficacy of BHV-4157 (200 mg once daily) versus placebo after 48 weeks of treatment in subjects with spinocerebellar ataxia (SCA).

Example 3

This example describes a further analysis of the study of Example 1. SASA scores were obtained and are reported in

| Condition | Intervention | Phase |
|---|---|---|
| Spinocerebellar Ataxias | Drug: troriluzole | Phase 3 |
| Spinocerebellar Ataxia Type 1 | Drug: Placebos | |
| Spinocerebellar Ataxia Type 2 | | |
| Spinocerebellar Ataxia Type 3 | | |
| Spinocerebellar Ataxia Type 6 | | |
| Spinocerebellar Ataxia Type 7 | | |
| Spinocerebellar Ataxia Type 8 | | |
| Spinocerebellar Ataxia Type 10 | | |

Study Type: Interventional
Study Design: Allocation: Randomized
  Intervention Model: Parallel Assignment
  Masking: Triple (Participant, Care Provider, Investigator)
  Primary Purpose: Treatment
Official Title: A Phase III, Long Term, Randomized, Double-blind, Placebo-controlled Trial of BHV-4157 in Adult Subjects With Spinocerebellar Ataxia
Primary Outcome Measures:
  1. Change in the total score of the Modified Scale for the Assessment and Rating of Ataxia (SARA) BHV-4157 versus placebo on ataxia symptoms in subjects with spinocerebellar ataxia (SCA) Type 1 and Type 2, after 48 weeks of treatment.
An increase in the total score indicates a worsening of symptoms. Change in the total score of the Modified Scale for the Assessment and Rating of Ataxia (SARA) BHV-4157 versus placebo on ataxia symptoms in subjects with spinocerebellar ataxia (SCA) Type 1 and Type 2, after 48 weeks of treatment.
Secondary Outcome Measures:
  2. Change of total score as measured by the Modified Scale for the Assessment and Rating of Ataxia of BHV-4157 versus placebo on ataxia symptoms in subjects with spinocerebellar ataxia (SCA) of any genotype after 48 weeks of treatment
An increase in the total score indicates a worsening of symptoms. Change of total score as measured by the Modified Scale for the Assessment and Rating of Ataxia of BHV-4157 versus placebo on ataxia symptoms in subjects with spinocerebellar ataxia (SCA) of any genotype after 48 weeks of treatment. [Time Frame: Baseline to week 48]
  3. To assess of the safety and tolerability of BHV-4157 in subjects with SCA by measuring the frequency and severity of adverse events and discontinuations due to adverse events. [Time Frame: Baseline to week 48]
  4. Measure the change in total score of BHV-4157 versus placebo on patient impression of benefit via use of the Patient Impression of Function and Activities of Daily Living Scale (PIFAS).
An increase in the total score indicates a worsening of symptoms. Measure the change in total score of BHV-4157 versus placebo on patient impression of benefit via use of the Patient Impression of Function and Activities of Daily Living Scale (PIFAS). [Time Frame: Baseline to week 48]
  5. Measure the change in the Neuro-QOL Fatigue Scale comparing BHV-4157 versus placebo on daily fatigue and activities.
A decrease in the total score indicates a worsening of symptoms. Measure the change in the Neuro-QOL Fatigue Scale comparing BHV-4157 versus placebo on daily fatigue and activities. [Time Frame: Baseline to week 48]
  6. To measure the change on upper extremity function and activities as measured by the Neuro-QOL Upper Extremity Scale for BHV-4157 versus placebo
A decrease in the total score indicates a worsening of symptoms. To measure the change on upper extremity function and activities as measured by the Neuro-QOL Upper Extremity Scale for BHV-4157 versus placebo. [Time Frame: Baseline to week 48]
  7. To measure the change on lower extremity mobility and activities as measured by the Neuro-QOL Lower extremity mobility scale for cBHV-4157 versus placebo.
A decrease in the total score indicates a worsening of symptoms. To measure the change on lower extremity mobility and activities as measured by the Neuro-QOL Lower extremity mobility scale for cBHV-4157 versus placebo. [Time Frame: Baseline to week 48]
  8. To measure the change over time comparing BHV-4157 versus placebo on the clinician impression of global functioning via use of the Clinical Global Impression-Global Improvement Scale (CGI-I)
An increase in the total score indicates a worsening of symptoms. To measure the change over time comparing BHV-4157 versus placebo on the clinician impression of global functioning via use of the Clinical Global Impression-Global Improvement Scale (CGI-I). [Time Frame: Baseline to week 48]
  9. To measure the change over time comparing BHV-4157 versus placebo on patient impression of global functioning as measured by the Patient Global Impression Scale (PGI)
A decrease in the total score indicates a worsening of symptoms. To measure the change over time comparing BHV-4157 versus placebo on patient impression of global functioning as measured by the Patient Global Impression Scale (PGI). [Time Frame: Baseline to week 48]
  10. Compare the change of activities of daily living as measured by the Activities of Daily Living Scale from the Friedreich's Ataxia Rating Scale (FARS-ADL) for BHV-4157 versus placebo
An increase in the total score indicates a worsening of symptoms. Compare the change of activities of daily living as measured by the Activities of Daily Living Scale from the Friedreich's Ataxia Rating Scale (FARS-ADL) for BHV-4157 versus placebo. [Time Frame: Baseline to week 48]
  11. To measure the change on daily functioning using the Functional Staging for Ataxia Scale from the Friedreich's Ataxia Rating Scale (FARS-FUNC) for BHV-4157 versus placebo
An increase in the total score indicates a worsening of symptoms. To measure the change on daily functioning using the Functional Staging for Ataxia Scale from the Friedreich's Ataxia Rating Scale (FARS-FUNC) for BHV-4157 versus placebo. [Time Frame: Baseline to week 48]

| Estimated Enrollment: 230 participants | |
|---|---|
| Arms | Interventions/treatment |
| Experimental: Arm 1: BHV-4157 BHV-4157/troriluzole 200 mg PO | Drug: troriluzole 200 mg PO |
| Placebo Comparator: Arm 2: Placebo Placebo 200 mg PO | Drug: Placebos 200 mg PO |
| Eligibility | |
| Ages Eligible for Study: | 18 Years to 75 Years (Adult, Older Adult) |
| Sexes Eligible for Study: | All |
| Accepts Healthy Volunteers: | No |

Criteria
Inclusion Criteria:
a. Subjects with a known or suspected diagnosis of the following specific hereditary ataxias: SCA1, SCA2, SCA3, SCA6, SCA7, SCA8 and SCA10.
i. A subject has clinical evidence that supports diagnosis of one of the aforementioned SCA genotypes but does not have producible test results from a CLIA certified lab from either a family member or for his or herself and the subject must be willing to undergo such testing to confirm the SCA diagnosis (in this case, site must wait for results of genotypic testing prior to randomization). b. Ability to ambulate 8 meters without human assistance (canes and other devices allowed).
c. Screening total SARA score ≥8. d. Determined by the investigator to be medically stable at Baseline/randomization as assessed by medical history, physical examination, laboratory test results, and electrocardiogram testing. Subjects must be physically able and expected to complete the trial as designed.
e. Subjects must have adequate hearing, vision, and language skills to perform SARA ratings and other neuropsychiatric testing and interviews as specified in the protocol.
Exclusion Criteria:
1. MMSE score <24.
2. Any medical condition other than one of the hereditary ataxias specified in the inclusion criteria that could predominantly significantly to the subjects' symptoms of ataxia (for example, alcoholism, vitamin deficiencies, multiple sclerosis, vascular disease, tumors, paraneoplastic disease, head injury, idiopathic late onset ataxia, multisystem atrophy) or that can confound assessment of ataxia symptoms (for example, stroke, arthritis).
3. SARA total score of >30 points at screening.
4. Clinical history of stroke.
5. Immunocompromised subjects.
6. Active liver disease or a history of hepatic intolerance to medications that in the investigator's judgment, is medically significant.
Study Design and Results
The study is conducted according to protocols which can be developed by those skilled in the art. The study subjects are treated in accordance with the protocols and their condition is assessed in consideration of the primary and secondary outcome measures according to medical practice procedures known to those skilled in the art.

Example 5

A drug product in the dosage form of a hard gelatin capsule for oral administration in a strength of 140 mg of BHV-4157 having a composition as set forth below is prepared by techniques known to those skilled in the art.

| Component | Function | Content per Capsule |
|---|---|---|
| Drug Substance | Active ingredient | 140 mg |
| Mannitol | Binder/Filler | 76.1 mg |
| Microcrystalline cellulose + dicalcium phosphate | Binder/Filler | 30.08 mg |
| Microcrystalline cellulose | Binder/Filler | 24.16 mg |
| Hydroxypropyl cellulose | Binder/Filler | 7.09 mg |
| Crospovidone | Disintegrant | 13.09 mg |
| Colloidal silicon dioxide | Glidant | 1.94 mg |
| Magnesium stearate (vegetable grade) | Lubricant | 1.94 mg |

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Those skilled in the art will recognize, or be able to ascertain using no more than routine experimentation, numerous equivalents to the specific procedures described herein. Such equivalents are considered to be within the scope of this invention and are covered by the following claims. For example, it is intended in accordance with the present invention that combination therapy using a riluzole prodrug and other therapeutic agents can be employed to treat ataxia and other associated diseases. Further, riluzole prodrugs other than those specifically disclosed in the description and Examples herein can be employed. Furthermore, it is intended that specific items within lists of items, or subset groups of items within larger groups of items, can be combined with other specific items, subset groups of items or larger groups of items whether or not there is a specific disclosure herein identifying such a combination.

What is claimed is:

1. A method of treating spinocerebellar ataxia type 3 in a patient, comprising administering to the patient in need of such treatment a therapeutically effective amount of a riluzole prodrug having the following formula:

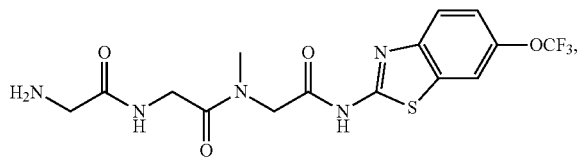 [SMILES: CN(CC(=O)Nc1nc2ccc(OC(F)(F)F)cc2s1)C(=O)CNC(=O)CN]

or a pharmaceutically acceptable salt thereof.

2. The method of claim 1, wherein the treatment provides an improvement in the patient's total SARA score of at least 0.8, or 0.9, or 1.0, or 1.1, or 1.2, or 1.3, or 1.4, or 1.5, or 1.6, or 1.7, or 1.8, or 1.9, or 2.0, or greater.

3. The method of claim 1, wherein the riluzole prodrug is administered to the patient at a dosage of from about 17.5 to 200 mg per day.

4. The method of claim 3, wherein the riluzole prodrug is administered to the patient at a dosage of about 17.5, or 35, or 70, or 100, or 140, or 200 mg per day.

5. The method of claim 4, wherein the riluzole prodrug is administered to the patient at a dosage of 200 mg, once per day.

6. The method of claim 4, wherein the riluzole prodrug is administered to the patient at a dosage of 140 mg, once per day.

7. The method of claim 1, wherein the riluzole prodrug is administered to the patient once per day.

8. The method of claim 1, wherein the riluzole prodrug is administered to the patient twice per day.

9. The method of claim 1, wherein the riluzole prodrug is administered to the patient in the form of a capsule.

10. The method of claim 1, wherein the riluzole prodrug is administered to the patient in the form of a tablet.

11. The method of claim 1, wherein the riluzole prodrug is administered to the patient for a duration of from about 8 weeks to 48 weeks.

12. The method of claim 1, wherein the riluzole prodrug is administered to the patient at a dosage of about 200 mg or less per day.

13. The method of claim 1, wherein the riluzole prodrug is administered to the patient once daily.

* * * * *